June 12, 1973 J. L. MOSSHOLDER Plant Pat. 3,355
AZALEA PLANT
Filed Nov. 8, 1971
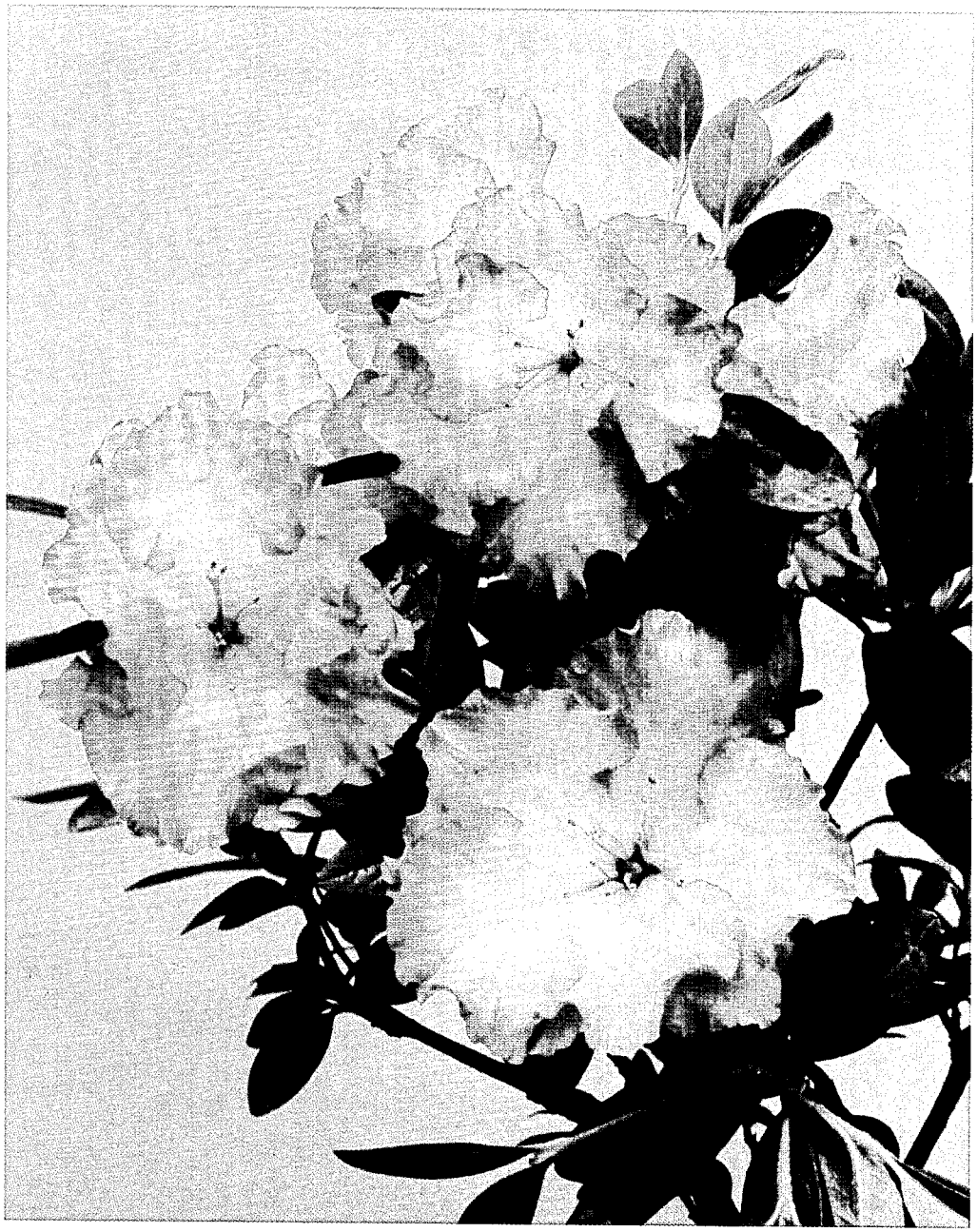

United States Patent Office

Plant Pat. 3,355
Patented June 12, 1973

3,355

AZALEA PLANT

Joseph L. Mossholder, 5547 5th St.,
Fallbrook, Calif. 92028

Filed Nov. 8, 1971, Ser. No. 196,701
Int. Cl. A01h *5/00*
U.S. Cl. Plt.—55 1 Claim This invention relates to a new and distinct variety of azalea plant.

This new variety of azalea plant has been obtained as a sport of an azalea plant referred to as the Easter Parade azalea as shown and described in the Bristow Plant Patent 1,707 issued May 13, 1958 and titled "Azalea Plant." The entire disclosure of this Plant Patent 1,707 is incorporated therein by reference.

The new variety of azalea plant has been asexually reproduced at Fallbrook, San Diego County, Calif., from its own cuttings a sufficient number of times so as to clearly show that the various characteristics of this plant as set forth in this specification are permanently fixed.

The accompanying illustration shows a portion of the azalea plant of this invention in bloom. All portions of the azalea plant of the invention which are not illustrated are as shown and described in the aforenoted Plant Patent 1,707. It has the general growth characteristics of the azalea plant described in this Plant Patent 1,707.

The new azalea plant of the present invention is distinctive in the characteristics of the flowers of this plant. More specifically it is considered to be distinguished from prior azalea plants and particularly the azalea plant shown in the Plant Patent 1,707 by virtue of the shape of its flower and the color characteristics of the flower ranging from a yellow shade to a pink and then a rose shade as indicated in the subsequent portions of this specification.

The following is a detailed description of the new azalea plant of this invention, its foliage and its flower:

*Plant*

Form of plant: Exceptionally bushy and compact; symmetrical. Even if plan is not regularly pinched or pruned, it will grow compactly and bushy.
Growth habit: A fast grower.
Rooting: Roots well; strong grower on its own roots; very vigorous.
Blooming habit: Prolific.
Blooming season: Later than almost all other related azaleas; late April or early May.
Suitability for forcing: Exceptional as a late forcing variety.

*Foliage*

Size: Mature leaves average 2" in length by ¾" wide.
Quantity: Abundant.
Color: New foliage—upper side, light green, glossy; under side, light green, flat. Old foliage—upper side, exceptionally dark green, glossy; under side, light green, semi-glossy.
Shape: Oval shaped; very slightly pointed.
Texture: Normal.
Edge or margin: Smooth.
Ribs and veins: More prominent than average.
Aspect: Large deep green, glossy foliage; abundant.

*Flower*

Size: Average 3" to 3½" across.
Flowers born: Average 3 on a stem; sometimes 2, occasionally 4.
Quantity of bloom: Abundant.
Continuity: Flowers hold well.
Petalage:
*Size.*—Average 1½" wide; 2" to 2¼" long on inside hose or cycles of petals. Average 1¼" wide by 1½" long on outside hose or cycle of petals.
*Number of petals under normal condition.*—5 on inside cycle; 5 on outside cycle.
*Color of bud.*—First showing is a rose color—Swiss rose #394 from the Plochere color system and including some Azalea color #395 from the Plochere color system and some pink color #304 from the Plochere color system.
*Color of the open flower.*—A misted yellow speckling at the throat of the flower appearing as #76 from the Plochere color system leading to an opera pink #304 from the Plochere color system surrounding the center of the throat portion. This pink blends into an Azalea #395 from the Plochere color system which surrounds it. This shading in turn leads to a rose edge on the periphery of the petals of the flower, this rose being Swiss rose #394 from the Plochere color system.
*Texture.*—Smooth.
Appearance: Hose-in-hose flower, usually with a slight separation between hoses or layers of petals. Inside hose is moderately ruffled at edge of flower; outside hose or layer slightly smaller than inside and not as ruffled. Individual petals of outside hose asymmetrically shaped, varying from a few near perfect to various interesting mutations. A single petal or outside usually appears to be two or three (occasionally more) petals because of its irregular edge. Some of flowers are hose-in-hose semi-double due to petaloids on some of stamens.
Shape: A ruffled hose-in-hose wide opening flower.
Arrangement: Average 3, sometimes 2 and sometimes 4, on each stem.
Persistence: Sets buds regularly every year.

*Reproductive organs*

*Stamens*: Normal; 7 to 9
*Anther.*—Normal, light brown.
*Filament.*—Pink
Pollen: Yellow; small amount of pollen.
Pistil: Normal.
*Style.*—Pink
*Stigma.*—Yellow with pink veins.
Ovary: Normal, slightly larger than average.

Having illustrated and described the invention or discovery, what is claimed as new and patentable is:

1. A distinct and new variety of azalea plant, substantially as illustrated and described hereinabove, and characterized generally by its unusual colors of its flowers, these flowers having a yellow speckled throat leading to a pink to an azalea and finally to a rose outer edge, the plant otherwise having the characteristics of an azalea plant as set forth and claimed in the Plant Patent 1,707.

No references cited.

ROBERT E. BAGWILL, Primary Examiner